United States Patent [19]

Ozawa et al.

[11] Patent Number: 5,396,008
[45] Date of Patent: Mar. 7, 1995

[54] PROCESS FOR PRODUCTION OF DIMETHYLTETRALIN

[75] Inventors: Shinji Ozawa; Makoto Takagawa; Kenji, all of Inamasa, Tsukuba, Japan

[73] Assignee: Mitsubishi Gas Chemical Co., Inc., Tokyo, Japan

[21] Appl. No.: 89,125

[22] Filed: Jul. 9, 1993

[30] Foreign Application Priority Data

Aug. 3, 1992 [JP] Japan .................. 4-206476

[51] Int. Cl.⁶ .............................. C07C 5/22
[52] U.S. Cl. .................. 585/411; 585/320; 585/410
[58] Field of Search .............. 585/320, 410, 411

[56] References Cited

U.S. PATENT DOCUMENTS

| | | | |
|---|---|---|---|
| 3,775,496 | 11/1973 | Thompson | 585/320 |
| 4,950,825 | 8/1990 | Sikkenga et al. | 585/320 |
| 5,008,479 | 4/1991 | Abe et al. | |
| 5,030,701 | 7/1991 | Sikkenga et al. | 585/320 |

FOREIGN PATENT DOCUMENTS 0351074  1/1990  European Pat. Off. .

OTHER PUBLICATIONS

Chemical Abstracts, vol. 80, No. 17, 29 Apr. 1974, abstract No. 95601k, p. 382, of JP-A-396,577.
Chemical Abstracts, vol. 83, No. 23, 8 Dec. 1975, abstract No. 192938v, p. 427, of JP-A-593,956.

*Primary Examiner*—Asok Pal
*Attorney, Agent, or Firm*—Frishauf, Holtz, Goodman & Woodward

[57] ABSTRACT

There is disclosed a process for producing dimethyltetralin consisting of 1,5-, 1,6- and 2,6-dimethyltetralin which comprises cyclizing 5-tolyl-penta-2-ene in gaseous state in the presence of diluent by the use of a catalyst comprising a crystalline aluminosilicate and a carrier and optionally a molding assistant. The abovementioned process is capable of producing industrially useful dimethyltetralin as the starting raw material for dimethylnaphthalene with high yield and high selectivity with minimized side reactions over a long stabilized period.

14 Claims, No Drawings

PROCESS FOR PRODUCTION OF DIMETHYLTETRALIN

BACKGROUND OF THE INVENTION

1. Field of the Invention

The present invention relates to a process for producing dimethyltetralin. More particularly, it relates to a process for producing dimethyltetralin with a high yield over a long stabilized period by the cyclization of the corresponding 5-tolyl-penta-2-ene under specific reaction conditions by the use of a specific catalyst. Dimethylnaphthalene (hereinafter sometimes abbreviated as "DMN") which is obtained by the dehydrogenation of dimethyltetralin is a compound of utmost importance as a starting raw material for naphthalene dicarboxylic acid to be used in the production of plastics such as polyesters. For example, polyethylene-2,6-naphthalate which is produced from 2,6-naphthalene dicarboxylic acid and ethylene glycol has heat resistance and mechanical properties more favorable than polyethylene terephthalate and is used for producing films and fibers.

2. Description of the Related Arts

Isomerically high purity is required not only for naphthalene dicarboxylic acid as a starting "raw material for plastics but also for DMN as the starting raw material for the aforementioned acid. Specifically, DMN has 10 isomers according to the positions of methyl groups, 1,2-; 1,3-; 1,4-; 1,5-; 1,6-; 1,7-; 1,8-; 2,3-; 2,6-; and 2,7-DMN and, when used as the starting raw material for naphthalene dicarboxylic acid, it is required to be a specific highly pure DMN free from other position isomers.

As a process for producing DMN, there is available an isolation process from a high boiling fraction from petroleum refining or from the tar fraction of coal origin, naphthalene alkylation process, synthetic process using an alkylbenzene and an olefin and the like.

In the case of an isolation process from a high boiling fraction from petroleum refining or the tar fraction of coal origin, the DMN contained in each of the fractions is a mixture of various DMN isomers and therefore requires an isomerization step and troublesome isolation process for the purpose of obtaining a specific desired DMN from among the isomer mixture. With regard to isomerization, it is known that the above-mentioned 10 isomers are classified into 4 groups as mentioned hereinbelow and that the isomerization in the same group is relatively easy, whereas that among different groups is difficult. In addition, it is extremely difficult to isolate a specific desired DMN from various DMN isomers. Furthermore, a variety of components other than DMN that are contained in the above-mentioned fractions makes it extremely difficult to isolate and recover a specific desired DMN with high purity from the mixture of DMN and the others.

Group A 1,5-DMN; 1,6-DMN; and 2,6-DMN
Group B 1,7-DMN; 1,8-DMN; and 2,7-DMN
Group C 1,3-DMN; 2,3-DMN; and 1,4-DMN
Group D 1,2-DMN The alkylation process of naphthalene is put into practice usually using a solid acid as a catalyst such as zeolite and silica-alumina. The process, however, involves the problems in that there are produced monomethylnaphthalene, trimethylnaphthalene, etc. other than DMN, a high selectivity to DMN is not attained and the resultant DMN is a mixture of a number of isomers. Accordingly, the process makes it difficult to afford the specific desired DMN in high yield as is the case with the isolation process from a high boiling fraction from petroleum refining or the tar fraction from coal origin.

As a countermeasure against the aforementioned problems, there is available a process for producing a specific DMN from an alkylbenzene and an olefin through multistage steps, exemplified by Japanese Patent Application Laid-Open No. 96540/1990 in which 2,6-DMN is produced from m-xylene, propylene and carbon monoxide and U.S. Pat. No. 5,008,479 in which 2,6-DMN is produced from toluene, butene and carbon monoxide.

Similarly, Japanese Patent Application Laid-Open Nos. 134634/1974, 89353/1975 and 67261/1973 disclose a process for producing 5-(o-tolyl)-penta-2-ene from o-xylene and butadiene, a process for producing 1,5-dimethyltetralin by cyclizing 5-(o-tolyl)-penta-2-ene and a process for producing 1,5-DMN by dehydrogenating 1,5-dimethyltetralin, respectively. The combination of the above-disclosed processes enables the production of 1,5-DMN with isomerically high purity from o-xylene and butadiene.

Japanese Patent Application Laid-Open No. 503389/1989 discloses a process for producing highly pure 2,6-DMN by isomerizing 1,5-DMN into the mixture of 1,5-DMN, 1,6-DMN and 2,6-DMN, which mixture is crystallized into the objective 2,6-DMN. The aforesaid process is highly advantageous in that isomerization and crystallization are carried out among 3 DMN isomers belonging to the same group as compared with those among the isomers belonging to different groups.

2,6-DMN has attracted the highest attention recently among the DMN isomers as the starting raw material for 2,6-naphthalene dicarboxylic acid. Thus the emergence of a process for industrially producing 2,6-DMN is eagerly desired.

The aforesaid Japanese Patent Application Laid-Open No. 134634/1974 also discloses a process for producing 5-(p-tolyl)-penta-2-ene from p-xylene and butadiene. In this case, it is presumed that 1,7-DMN is obtained by the successive cyclization and dehydrogenation, 2,7-DMN is obtained in high purity by further isomerization and crystalization, and also the use of m-xylene enables the production of the mixture of 1,6-DMN and 1,8-DMN.

It can be said that the process for producing DMN by the use of xylene and butadiene as starting raw materials is industrially excellent, since it enables the production of a specific DMN with isomerically high purity as described hereinbefore.

The process for producing DMN from xylene and butadiene comprises the steps of synthesizing 5-tolyl-penta-2-ene by side-chain alkenylation, synthesizing dimethyltetralin by means of cyclization, synthesizing DMN by means of dehydrogenation, isomerizing DMN and crystalizing isolation. The synthesis of dimethyltetralin by cyclizing 5-tolyl-penta-2-ene is disclosed in Japanese Patent Application Laid-Open No. 93348/1974 in which is used a solid phosphoric acid as a catalyst and Japanese Patent Application Laid-Open No. 500052/1991 through PCT in which is employed as a catalyst a ultra-stabilized Y-type zeolite (USY zeolite) that is modified with platinum and copper, showing a yield of 95% or more in the working examples of both of the disclosures.

However, all the working examples turned out to be unfavorable with respect to the catalyst service life. The primary contributor to the shortened service life of the catalyst is the coking of the catalyst, which decreases the conversion efficiency of 5-tolyl-penta-2-ene. The decrease in the conversion efficiency of the starting raw material not only lowers the yield of the objective dimethyltetralin but also causes unreacted 5-tolyl-penta-2-ene to act as a catalyst poison in the following dehydrogenation step, thus further reducing the service life of the dehydrogenation catalyst.

With regard to the process for producing dimethyltetralin by the cyclization of the corresponding 5-tolyl-penta-2-ene, the conventional techniques as mentioned above suffer the disadvantage of shortened service life of the catalyst in spite of a high yield obtained.

Under such circumstances, intensive research and investigation were made by the present inventors in order to develop a process capable of producing dimethyltetralin with high conversion efficiency and high yield for a long-term stabilized period by the cyclization of the corresponding 5-tolyl-penta-2-ene. As a result, there have been found by the present inventors effective catalysts and a production process for the purpose. The present invention has been accomplished on the basis of the above-mentioned finding.

SUMMARY OF THE INVENTION

It is an object of the present invention to provide a process capable of producing dimethyltetralin with high conversion efficiency and high yield for a long-term stabilized period by the cyclization of the corresponding 5-tolyl-penta-2-ene.

It is another object of the present invention to proceed with the cyclization almost quantitatively at a relatively low reaction temperature.

It is still another object of the present invention to provide a catalyst capable of maintaining a high cyclization activity and performance and suppressing side reactions such as polymerization and decomposistion of the reactants.

Other objects of the present invention will be obvious from the description of this text hereinafter disclosed.

For the purpose of achieving the above-described object, the present invention provides a process for producing dimethyltetralin which comprises cyclizing 5-tolyl-penta-2-ene in gaseous state in the presence of a diluent by the use of a catalyst comprising a crystalline aluminosilicate and a carrier, and optionally a molding assistant.

DESCRIPTION OF PREFERRED EMBODIMENTS

The production of dimethyltetralin by the cyclization of the corresponding 5-tolyl-penta-2-ene is feasible by using a solid acid such as solid phosphoric acid, zeolite and silica-alumina as a catalyst, but the use of the solid-acid catalyst as such can not attain a favorable cyclization yield. The greatest cause for failure to attain a satisfactory cyclization yield is the polymerization of 5-tolyl-penta-2-ene as the starting raw material, and mention may be made of the decomposition thereof to accompany the polymerization as one of the contributors. The occurrence of the polymerization thereof brings about poisoning of the catalyst active point due to the high-boiling components as the byproducts, thus making it impossible to proceed with the reaction for a long time.

In view of the above, an investigation was conducted by the present inventors on the development of a method for suppressing the side reactions such as polymerization and decomposition while maintaining the high cyclization activity and performance of the solid-acid catalyst. As a result, it has been discovered that the side reactions are remarkable suppressed by a method wherein a crystalline aluminosilicate is combined with a substantially inactive carrier for the sufficient dispersion thereof and adjusting the ratio by weight of the aluminosilicate to the carrier. The present invention is founded on the above-mentioned discovery.

It is well known that the cyclization of 5-tolyl-penta-2-ene into the corresponding dimethyltetralin is an intramolecular alkylation reaction and that each of the reactions such as alkylation, polymerization and decomposition proceeds in the presence of an acid as a catalyst. Therefore, it has generally been regarded as being almost impossible to selectively proceed with a cyclizing reaction by the use of a solid acid as a catalyst while suppressing the side reactions such as polymerization and decomposition of the reactants. Nevertheless, the breakthrough in selective cyclizing reaction with supressed polymerization and decomposition by the combined use of a specific solid acid and a specific carrier makes the present invention highly significant from an industrial viewpoint.

The catalyst to be employed in the present invention comprises a crystalline aluminosilicate and a carrier.

Examples of the crystalline aluminosilicate to be used in the process of the present invention include mordenite, X-type zeolite and Y-type zeolite, among which are desirable mordenite, Y-type zeolite and ultra-stabilized Y-type zeolite (USY zeolite), and is particularly desirable mordenite. The desirable crystalline aluminosilicate is that of H-type.

The carrier to be employed in the process of the present invention needs to be capable of well dispersing the crystalline aluminosilicate. An strongly acidic carrier such as activated alumina is liable to cause side reactions such as polymerization and decomposition. Accordingly, the carrier is required to have a low reactivity with 5-tolyl-penta-2-ene. The carrier is desirably a non-acidic one or a weakly acidic one, such as carbon, silicon oxide, titanium oxide, zirconium oxide and mixture thereof among which carbon and silicon oxide are particularly desirable.

The ratio of the crystalline aluminosilicate to the carrier is 0.01 to 0.5, preferably 0.02 to 0.3 part by weight per one (1) part by weight of the carrier. An excessively large amount of the aluminosilicate is liable to cause side reactions such as polymerization and decomposition, whereas an unreasonably small amount thereof unfavorably lowers the reactivity of 5-tolyl-penta-2-ene.

The method of preparing the catalyst for the process of the present invention is not specifically limited insofar as the method is capable of well dispersing the crystalline aluminosilicate and the carrier in the catalyst to be prepared, but is exemplified by a method wherein the crystalline aluminosilicate is mixed with the carrier to form a slurry state and the resultant mixture in the form of slurry is dried and calcined or fired.

The catalyst is usable in the form of a powder in the process of the present invention, but is preferably in the form of a molding according to the reaction method. In the case where a component other than the above is employed for the purpose of molding, alumina, silica or mixture thereof is suitable and alumina is particularly suitable as the molding assistant. In general, clays are widely used in addition to alumina or silica for molding a crystalline aluminosilicate, but are unsuitable for the catalyst according to present invention. Specifically, the molded catalyst by the use of a clay results in failure to maintain the high activity of the catalyst for a long period, whereas the molded catalyst using alumina or silica is able to do so in a stable manner. A large usage of alumina or silica, however, is apt to bring about side reactions. Thus, the amount of alumina or silica to be used as the molding assistant is desirably 20% or less by weight based on the total of the crystalline aluminosilicate and the carrier.

Having extremely high activity and high selectivity, the catalyst according to the present invention is suited to produce dimethyltetralin from the corresponding 5-tolyl-penta-2-ene with high yield, however, it is an indispensable condition to carry out the cyclizing reaction in a gas phase. Specifically, the present reaction in a liquid phase leads to considerable dimerization reaction of 5-toyly-penta-2-ene along with the cyclizing reaction thereof, whereas the reaction in gas phase can almost completely suppress the dimerization of 5-tolyl-penta-2-ene, thus enabling dimethyltetralin to be produced with high yield. The abovementioned discovery constitutes one of the outstanding features of the process according to the present invention.

Japanese Patent Application Laid-Open No. 500052/1991 through PCT describes that about 400 hours of stable reaction results are obtained by carrying out the cyclizing reaction of 5-tolyl-penta-2-ene in the liquid phase in the production of dimethyltetralin. Such stable reaction result is presumably due to the effect that the starting raw material or the reaction product washes away the cokes produced during the course of reaction or the precursor thereof. Consequently, it is generally thought that it is preferable to carry out the reaction in liquid phase from the viewpoint of catalyst service life.

Nevertheless, the above-mentioned conventional principle is not applicable to the catalyst for the process of the present invention. The implementation of the reaction in the gas phase is the only way of almost completely suppressing the dimerization of 5-tolyl-penta-2-ene and maintaining the high activity of the catalyst over a long-term stabilized period as far as the present invention is concerned.

The applicable method of effecting the reaction in the gas-phase in the process of the present invention is exemplified by a method in which the partial pressures of the starting raw material and the reaction product are decreased with a diluent and a pressure reducing method, of which the former is preferable.

The diluent is not specifically limited insofar as it is inactive under the reaction conditions and capable of maintaining the reaction system in a gas-phase state, but is exemplified by gaseous substances such as nitrogen, carbon dioxide, hydrogen, argon or helium; saturated aliphatic hydrocarbons such as propane, butane, pentane, hexane or heptane; alicyclic hydrocarbons such as cyclopentane, cyclohexane and methylcyclohexane; and aromatic hydrocarbons such as benzene, toluene and xylene. The diluent can be used singly or in combination.

The amount of the diluent must be sufficient for maintaining the reaction system in the gas phase, and it depends upon the reaction pressure, reaction temperature, and the sort of the diluent. Among them, reaction pressure and reaction temperature have great influence on the amount necessary to keep the reaction system in the gas phase. The inventors have made an intensive effort to elucidate the dependence of the diluent amount necessitated upon reaction pressure and temperature and have found that when the mole ratio of the diluent to 5-tolyl-penta-2-ene is larger than the value estimated by the following equation, the whole reaction system is in the gas phase and significant results can be stably obtained for a long period of time.

When the raw material 5-tolyl-penta-2-ene includes, as impurities, substances having a lower boiling point than 5- tolyl-penta-2-ene, they should be accounted as a part of the diluent.

$$\frac{P}{\exp(0.03T - 0.35)} + 1$$

where;

P is the reaction pressure in mmHg-absolute

T is the reaction temperature in degrees Celsius.

According to the above-described empirical equation, under the conditions of atmospheric pressure and 170° C., the mole ratio of the diluent to 5-tolyl-penta-2-ene should be 8 or more, preferably 10 is recommended.

Since the present reaction is exothermic one accompanied with a heat generation of about 22 kcal/mol, the use of the diluent is desirable from the standpoint of heat removal.

An excessive amount of the diluent does not cause any problem from the viewpoint of maintaining the reaction system in gas phase and removing the heat of reaction, but is economically unfavorable because of the increasing circulation amount of the diluent. Accordingly, the amount of the diluent in practical use should be determined taking the aforesaid factors into consideration.

The reaction method applicable to the implementation of cyclization reaction of 5-tolyl-penta-2-ene by using the catalyst according to the present invention is not specifically limited, but may be any of batchwise and continuous systems.

Likewise, the reaction equipment is not specifically limited, but may be selected from a fixed-bed system, a moving-bed system and a fluidized-bed system, among which the fixed-bed system is preferable from the operational convenience.

The reaction temperature for performing the process of the present invention is in the range of 100 to 400° C., preferably 150 to 300° C. A reaction temperature higher than the upper limit results in liability to the polymerization of 5-tolyl-penta-2-ene accompanying the objective reaction and to the isomerization of the produced dimethyltetralin, thereby causing failure to produce the specific DMN with high yield from the dimethyltetralin. On the contrary, a reaction temperature lower than the lower limit leads to lowering in the conversion efficiency of 5-tolyl-penta-2-ene, thus causing failure to produce dimethyltetralin with high yield.

The feed rate of starting raw material per unit weight of the catalyst in performing the process of the present invention varies depending on the form of the reaction and, in the case of fixed-bed flow system, it is 0.1 to 5 $hr^{-1}$, preferably 0.3 to 2.5 $hr^{-1}$ expressed in terms of WHSV (weight hourly space velocity).

In summary, the process according to the present invention enables the production of the objective dimethyltetralin with high yield for a long-term stabilized period from the corresponding 5-toyly-penta-2-ene as a starting raw material, thereby rendering itself highly significant from the industrial point of view.

In the following, the present invention will be described in more detail with reference to the examples and comparative examples, which examples shall not be construed to limit the present invention thereto.

In Examples 1 to 9 and Comparative Examples 1 to 6, 20 g of the catalyst prepared in each of the examples and comparative examples was packed in a quartz-made tubular reactor with 20 mm inside diameter and the reaction was carried out at atmospheric pressure. The results obtained are given in Tables 1 to 11.

In each of the examples, the conversion efficiency of 5-(o-tolyl)-penta-2-ene as a starting raw material is unexceptionally 100%, and the catalyst prepared in each of the examples contributed to the high yield of dimethyltetraline maintained for a long period of time as well as to the high proportion of 1,5-dimethyltetralin to dimethyltetralin.

As opposed to the examples, dimethyltetralin in each of the comparative examples was produced with low yield, or even with high yield it was accompanied with a large amount of dimethyltetralin other than 1,5-, 1,6- or 2,6-dimethyltetralin.

In the following, dimethyltetralin is abbreviated to "DMT".

EXAMPLE 1

In a stainless steel-made vessel were placed 15 g of mordenite available in the market (H-type, produced by Tosoh Corporation), 270 g of silica and 21 g of alumina sol with alumina content of 70% by weight as a binder, and 500 g of pure water was added to the mixture with sufficient mixing and stirring at room temperature. Thereafter the aqueous mixture was molded with an extruder, dried at 110° C., calcined or fired at 350° C. for 3 hours to prepare a catalyst. The cyclizing reaction was put into practice by the use of the catalyst thus obtained under the conditions including atmospheric reaction pressure, 170° C. reaction temperature, 24 g/hour feed rate of 5-(o-tolyl)-penta-2-ene as a starting raw material, 600 cc/min. feed rate of nitrogen as a diluent and 11 molar ratio of the diluent to the starting raw material. The results are given in Table 1.

EXAMPLE 2

The catalyst was prepared in the same manner as in Example 1 except that there were used 10 g of the mordenite available on the market (H-type, produced by Tosoh Corporation) and 320 g of silica.

The cyclizing reaction was put into practice by the use of the catalyst thus obtained under the conditions including atmospheric reaction pressure, 150° C. reaction temperature, 24 g/hour feed rate of 5-(o-tolyl)-penta-2-ene as a starting raw material, 1400 cc/min. feed rate of nitrogen as a diluent and 25 molar ratio of the diluent to the starting raw material. The results are given in Table 2.

EXAMPLE 3

The catalyst was prepared in the same manner as in Example 1 except that there were used 10 g of the USY zeolite available on the market (H-type, produced by Tosoh Corporation), 550 g of silica and 41 g of alumina sol with alumina content of 70% by weight as a binder. The cyclizing reaction was put into practice by the use of the catalyst thus obtained under the conditions including atmospheric reaction pressure, 160° C. reaction temperature, 24 g/hour feed rate of 5-(o-tolyl)-penta-2-ene as a starting raw material, 1000 cc/min. feed rate of nitrogen as a diluent and 18 molar ratio of the diluent to the starting raw material. The results are given in Table 3.

EXAMPLE 4

The catalyst was prepared in the same manner as in Example 1 except that there were used 10 g of the USY zeolite available on the market (H-type, produced by Tosoh Corporation), 550 g of silica and 160 g of silica sol with silica content of 25% by weigh as a binder. The cyclizing reaction was put into practice by the use of the catalyst thus obtained under the conditions including atmospheric reaction pressure, 190° C. reaction temperature, 40 g/hour feed rate of 5-(o-tolyl)-penta-2-ene as a starting raw material, 560 cc/min. feed rate of nitrogen as a diluent and 6 molar ratio of the diluent to the starting raw material. The results are given in Table 4.

EXAMPLE 5

The catalyst was prepared in the same manner as in Example 1 except that there were used 10 g of the USY zeolite available on the market (It-type, produced by Tosoh Corporation), 550 g of activated carbon and 41 g of alumina sol with alumina content of 70% by weigh as a binder. The cyclizing reaction was put into practice by the use of the catalyst thus obtained under the conditions including atmospheric reaction pressure, 180° C. reaction temperature, 24 g/hour feed rate of 5-(o-tolyl)-penta-2-ene as a starting raw material, 500 cc/min. feed rate of nitrogen as a diluent and 9 molar ratio of the diluent to the starting raw material. The results are given in Table 5.

EXAMPLE 6

The catalyst was prepared in the same manner as in Example 1 except that there were used 81 g of the USY zeolite available on the market (H-type, produced by Tosoh Corporation), 550 g of titanium oxide and 120 g of alumina sol with alumina content of 70% by weight as a binder. The cyclizing reaction was put into practice by the use of the catalyst thus obtained under the conditions including atmospheric reaction pressure, 170° C. reaction temperature, 24 g/hour feed rate of 5-(o-tolyl)-penta-2-ene as a starting raw material, 600 cc/min. feed rate of nitrogen as a diluent and 11 molar ratio of the diluent to the starting raw material. The results are given in Table 6.

EXAMPLE 7

The procedure in Example 1 was repeated to cyclize 5-(o-tolyl)-penta-2-ene except that as the diluent, heptane in a molar amount of 10 times the starting raw material was used in place of nitrogen. The results are given in Table 7.

EXAMPLE 8

The procedure in Example 1 was repeated to cyclize 5-(o-tolyl)-penta-2-ene except that as the diluent, o-xylene in a molar amount of 10 times the starting raw material was used in place of nitrogen. The results are give in Table 8.

COMPARATIVE EXAMPLE 1

The procedure in Example 1 was repeated to cyclize 5-(o-tolyl)-penta-2-ene except that 20 g of USY-zeolite available on the market was used as such as the catalyst and the reaction temperature was set to 160° C.

Although 100% conversion efficiency of the starting raw material was obtained, a large amounts of dimethyltetralin isomers other than the objective 1,5-dimethyltetralin were contained in the cyclization product. The reaction results are given in Table 9.

COMPARATIVE EXAMPLE 2

The procedure in Example 1 was repeated to cyclize 5-(o-tolyl)-penta-2-ene except that 20 g of mordenite available on the market was used as such as the catalyst and the reaction temperature was set to 160° C.

The results are given in Table 10.

COMPARATIVE EXAMPLE 3

The procedure in Example 1 was repeated to cyclize 5-(o-tolyl)-penta-2-ene except that the use of diluent was omitted. Although 100% conversion efficiency of the starting raw material was obtained, the dimer of the starting raw material was formed in a proportion of 25% by weight. The results are given in Table 10.

COMPARATIVE EXAMPLE 4

The procedure in Example 1 was repeated to cyclize 5-(o-tolyl)-penta-2-ene except that the feed rate of nitrogen was set to 400 cc/min. (molar ratio thereof being 7.) The results are given in Table 10. Although 100% conversion efficiency of the starting material was obtained, the dimer of the starting raw material was formed in a proportion of 10% by weight.

COMPARATIVE EXAMPLE 5

The procedure in Example 1 was repeated to cyclize 5-(o-tolyl)-penta-2-ene except that 20 g of silica/alumina available on the market was used as such as the catalyst and the reaction temperature was set to 160° C. The results are given in Table 10. Although 100% conversion efficiency of the starting raw material was obtained, large amounts of dimethyltetralin isomers other than the objective 1,5-dimethyltetralin were contained in the cyclization product.

COMPARATIVE EXAMPLE 6

The procedure in Example 1 was repeated to cyclize 5-(o-tolyl)-penta-2-ene except that as the diluent, water in a molar amount of 10 times the starting raw material was used in place of nitrogen, and the reaction temperature was set to 135° C. As the result, although 100% conversion efficiency of the starting raw material was obtained, substantially all the starting raw material was converted into low-boiling components.

EXAMPLE 9

The procedure in Example 1 was repeated except that 5-(p-tolyl)-penta-2-ene was used in place of 5-(o-tolyl)-penta-2-ene. The results are given in Table 11. Thus, 100% conversion efficiency of the starting raw material was obtained.

TABLE 1

| Elapsed time from the start of reaction (hour) | Reaction temperature (°C.) | Sum of DMT and DMN | Composition of liquid reaction product (% by weight); concentration of isomers in DMT | | | | | Dimer of starting raw material | Low-boiling components |
|---|---|---|---|---|---|---|---|---|---|
| | | | (1,5- | 1,6- | 2,6- | Others) | DMN | | |
| 203 | 170 | 99.6 | 98.5 | 0.5 | 0.2 | 0 | 0.4 | 0 | 0.4 |
| 1604 | 170 | 98.9 | 98.2 | 0.3 | 0.1 | 0 | 0.3 | 0 | 1.1 |
| 2352 | 170 | 98.3 | 98.1 | 0.1 | 0.1 | 0 | 0 | 0 | 1.7 |

TABLE 2

| Elapsed time from the start of reaction (hour) | Reaction temperature (°C.) | Sum of DMT and DMN | Composition of liquid reaction product (% by weight); concentration of isomers in DMT | | | | | Dimer of starting raw material | Low-boiling components |
|---|---|---|---|---|---|---|---|---|---|
| | | | (1,5- | 1,6- | 2,6- | Others) | DMN | | |
| 356 | 150 | 99.0 | 97.6 | 0.3 | 0.1 | 0 | 1.0 | 0 | 1.0 |
| 1152 | 150 | 98.9 | 98.1 | 0.2 | 0.1 | 0 | 0.5 | 0 | 1.1 |
| 2604 | 150 | 98.5 | 98.3 | 0.1 | 0.1 | 0 | 0 | 0 | 1.5 |

TABLE 3

| Elapsed time from the start of reaction (hour) | Reaction temperature (°C.) | Sum of DMT and DMN | Composition of liquid reaction product (% by weight); concentration of isomers in DMT | | | | | Dimer of starting raw material | Low-boiling components |
|---|---|---|---|---|---|---|---|---|---|
| | | | (1,5- | 1,6- | 2,6- | Others) | DMN | | |
| 356 | 160 | 99.5 | 97.8 | 0.4 | 0.1 | 0 | 1.2 | 0 | 0.5 |
| 1052 | 160 | 98.8 | 97.7 | 0.2 | 0.1 | 0 | 0.8 | 0 | 1.2 |
| 2404 | 160 | 98.2 | 97.5 | 0.1 | 0.1 | 0 | 0.5 | 0 | 1.8 |

TABLE 4

Example 4

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 360 | 190 | 99.4 | 97.5 | 0.9 | 0.4 | 0 | 0.6 | 0 | 0.6 |
| 720 | 190 | 97.9 | 97.0 | 0.4 | 0.1 | 0 | 0.4 | 0 | 2.1 |
| 1080 | 190 | 96.9 | 96.5 | 0.1 | 0.1 | 0 | 0.2 | 0 | 3.1 |

TABLE 5

Example 5

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 384 | 180 | 99.0 | 93.0 | 0.6 | 0.4 | 0 | 5.0 | 0 | 1.0 |
| 864 | 180 | 97.6 | 92.6 | 0.3 | 0.2 | 0 | 4.5 | 0 | 2.4 |
| 1296 | 180 | 96.3 | 92.0 | 0.1 | 0.1 | 0 | 4.1 | 0 | 3.7 |

TABLE 6

Example 6

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 460 | 170 | 99.6 | 98.5 | 0.5 | 0.2 | 0 | 0.4 | 0 | 0.4 |
| 1035 | 170 | 99.1 | 98.4 | 0.3 | 0.1 | 0 | 0.3 | 0 | 0.9 |
| 1552 | 170 | 98.7 | 98.2 | 0.2 | 0.1 | 0 | 0.2 | 0 | 1.3 |

TABLE 7

Example 7

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 312 | 170 | 99.6 | 98.5 | 0.5 | 0.2 | 0 | 0.4 | 0 | 0.4 |
| 936 | 170 | 99.0 | 98.3 | 0.3 | 0.1 | 0 | 0.3 | 0 | 1.0 |
| 1404 | 170 | 98.5 | 98.1 | 0.1 | 0.1 | 0 | 0.2 | 0 | 1.5 |

TABLE 8

Example 8

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 399 | 170 | 99.6 | 98.5 | 0.5 | 0.2 | 0 | 0.4 | 0 | 0.4 |
| 1197 | 170 | 99.0 | 98.3 | 0.3 | 0.1 | 0 | 0.3 | 0 | 1.0 |
| 2394 | 170 | 98.5 | 98.1 | 0.1 | 0.1 | 0 | 0.2 | 0 | 1.5 |

TABLE 9

Comparative Example 1

| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| --- | --- | --- | --- | --- | --- | --- | --- | --- | --- |
| | | | (1,5- | 1,6- | 2,6- | Others) | | | |
| 120 | 160 | 93.0 | 31.0 | 20.7 | 10.3 | 27.6 | 3.4 | 1.0 | 6.0 |
| 192 | 160 | 92.9 | 56.0 | 10.4 | 7.6 | 16.4 | 2.5 | 1.1 | 6.0 |
| 312 | 160 | 92.8 | 75.6 | 5.7 | 2.7 | 6.5 | 2.3 | 0.9 | 6.3 |

TABLE 10

| | | | Comparative Example 2-5 | | | | | | |
|---|---|---|---|---|---|---|---|---|---|
| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| | | | (1,5- | 1,6- | 2,6- | Others) | | | |
| | | | Comparative Example 2 | | | | | | |
| 203 | 160 | 92.8 | 54.3 | 10.9 | 6.6 | 19.0 | 2.0 | 0.6 | 6.6 |
| | | | Comparative Example 3 | | | | | | |
| 203 | 160 | 72.7 | 70.5 | 0.6 | 0.4 | 0 | 1.2 | 25.0 | 2.3 |
| | | | Comparative Example 4 | | | | | | |
| 203 | 160 | 89.5 | 87.3 | 0.6 | 0.4 | 0 | 1.2 | 10.0 | 0.5 |
| | | | Comparative Example 5 | | | | | | |
| 203 | 160 | 91.5 | 70.9 | 5.6 | 3.4 | 10.4 | 1.2 | 4.0 | 4.5 |

TABLE 11

| | | | Example 9 | | | | | | |
|---|---|---|---|---|---|---|---|---|---|
| Elapsed time from the start of reaction (hour) | Reaction temperature (°C.) | Sum of DMT and DMN | Composition of liquid reaction product (% by weight); concentration of isomers in DMT | | | | DMN | Dimer of starting raw material | Low-boiling components |
| | | | (1,5- | 1,6- | 2,6- | Others) | | | |
| 108 | 160 | 99.0 | 97.5 | 0.6 | 0.4 | 0 | 0.5 | 0 | 1.0 |
| 1020 | 160 | 98.8 | 98.2 | 0.3 | 0.1 | 0 | 0.2 | 0 | 1.2 |
| 1703 | 160 | 98.5 | 98.1 | 0.1 | 0.1 | 0 | 0.2 | 0 | 1.5 |

What is claimed is:

1. A process for producing a dimethyltetralin product consisting essentially of 1,5-dimethyltetralin, 1,6-dimethyltetralin and 2,6-dimethyltetralin, which comprises cyclizing 5-tolyl-penta-2-ene in a gaseous state in the presence of a diluent with a catalyst comprising (i) a crystalline aluminosilicate selected from the group consisting of mordenite, X-type zeolite and Y-type zeolite and (ii) a carrier, the carrier being at least one member selected from the group consisting of carbon, silicon oxide, titanium oxide and zirconium oxide and the ratio of the crystalline aluminosilicate to the carrier is 0.01 to 0.5 by weight based on the carrier, a mole ratio of the diluent to the 5-tolyl-penta-2-ene as a starting material being larger than a value determined by the following equation: $(P/\exp(0.03\ T-0.35))+1$, wherein P is a reaction pressure in mmHg-absolute at which the cyclizing is carried out and T is a reaction temperature in °C. at which the cyclizing is carried out.

2. The process according to claim 1 wherein the catalyst further comprises at least one molding assistant selected from the group consisting of alumina and silica.

3. The process according to claim 1 wherein the crystalline aluminosilicate is Y-type zeolite which is ultra-stabilized Y-type zeolite.

4. The process according to claim 1 wherein the crystalline aluminosilicate is selected from the group consisting of H-type mordenite and H-type ultra-stabilized Y-type zeolite.

5. The process according to claim 1 wherein the cyclizing is carried out at a reaction temperature of 100° C. to 400° C.

6. The process according to claim 1 wherein the diluent is at least one member selected from the group consisting of nitrogen, carbon dioxide, hydrogen, argon and helium.

7. The process according to claim 1 wherein the diluent is at least one hydrocarbon selected from the group consisting of aliphatic hydrocarbons, alicyclic hydrocarbons and aromatic hydrocarbons.

8. The process according to claim 1 wherein the cyclizing reaction is carried out in a fixed bed system.

9. The process according to claim 4 wherein the carrier is selected from the group consisting of carbon and silicon oxide.

10. The process according to claim 9 wherein the ratio of the crystalline aluminosilicate to the carrier is 0.02 to 0.3 part by weight based on the carrier.

11. The process according to claim 2 wherein the alumina or silica is in an amount of 20 weight % or less based on the total of the crystalline aluminosilicate and the carrier.

12. The process according to claim 10 wherein the diluent is selected from the group consisting of nitrogen, carbon dioxide, hydrogen, argon, helium, propane, butane, pentane, hexane, heptane, cyclopentane, cyclohexane, methylcyclohexane, benzene, toluene, xylene and mixtures thereof.

13. The process according to claim 12 wherein the cyclizing is carried out at a temperature of 150 to 300° C.

14. The process according to claim 13 wherein the cyclizing is carried out at a temperature of 170° C., at atmospheric pressure and with a mole ratio of the diluent to the 5-tolyl-penta-2-ene of 8 to 10.

* * * * *